US007749494B2

(12) United States Patent
Renaud et al.

(10) Patent No.: US 7,749,494 B2
(45) Date of Patent: Jul. 6, 2010

(54) USE OF HYDROGENOTROPHIC ACETOGENIC STRAINS FOR PREVENTING OR TREATING DIGESTIVE DISORDERS

(75) Inventors: Michel Renaud, Le Cendre (FR); Annick Bernalier, La Roche-Blanche (FR)

(73) Assignee: Institut National de la Recherche Agronomique, Paris Cedex (FR)

( * ) Notice: Subject to any disclaimer, the term of this patent is extended or adjusted under 35 U.S.C. 154(b) by 941 days.

(21) Appl. No.: 10/275,706

(22) PCT Filed: May 11, 2001

(86) PCT No.: PCT/FR01/01426

§ 371 (c)(1),
(2), (4) Date: Feb. 6, 2003

(87) PCT Pub. No.: WO01/85187

PCT Pub. Date: Nov. 15, 2001

(65) Prior Publication Data

US 2003/0147858 A1    Aug. 7, 2003

(30) Foreign Application Priority Data

May 11, 2000    (FR)    ................................. 00 06009

(51) Int. Cl.
*A61K 45/00*    (2006.01)
*A01N 63/00*    (2006.01)
*A01N 63/02*    (2006.01)
(52) U.S. Cl. ...................... 424/93.4; 424/93.1; 435/822
(58) Field of Classification Search ................. 424/93.4
See application file for complete search history.

(56) References Cited

U.S. PATENT DOCUMENTS 6,348,452 B1 *    2/2002    Brown et al. ................... 514/60
6,645,530 B1 *    11/2003    Borody ........................ 424/543

FOREIGN PATENT DOCUMENTS

| DE | 19826928 A1 | 6/1998 |
| EP | 0778778 | 3/1996 |
| WO | WO 97/20577 | 6/1997 |
| WO | WO 9720577 | 6/1997 |
| WO | WO 98/55131 | 12/1998 |
| WO | WO9855131 | 12/1998 |

OTHER PUBLICATIONS

Joblin K N., "Ruminal Acetogens and Their Potential to Lower Remnant Methane Emissions." *Australian Journal of Agricultural Research*. vol. 50. No. 8. 1999, pp. 1307-1313. XP001010439.
Bernalier A et al., "Ruminococcus Hydrogenotrophicus sp. Nov . A New H-2/CO-2-Utilizing Acetogenic Bacterium Isolated From Human Feces." *Archives of Microbiology*, vol. 166. No. 3, 1996, pp. 176-183, XP000979148.
Keller et al.. "DNA Probes", 1994. Stockton Press. New York. XP002158943 108660 pp. 594-596.
Bernalier et al., "Acetogenesis from HO2 and CO-2 By Methane and Non-Methane-Producing Human Colonic Bacterial Communities" *Fems Microbiology Ecology*. vol. 19. No. 3. 1996. pp. 193-202. XP000979130.
Durand et al., "Reductive Acetogenesis in Animal and Human Gut." Physiological and Clinical Aspects of Short-Chain Fatty Acids, 1995. pp. 107-117, XP000979817 *Cambridge University Press* ISBN 0-521-44048-3.
Van Nevel et al., "Conrol of Rumen Methanogenesis." *Environmental Monitoring and Assessment*. vol. 42, 1996, pp. 73097, ? XP000979267.
O'Sullivan et al., "Bacterial Supplementation in the Irritable Bowel Syndrome. A Randomised Double-Blind Placebo-Controlled Cross-over Study", *Digest Liver Dis*. 2000. pp. 294-301.
Bernalier, A. et al., "*Ruminococcus hydrogenotrophicus* sp. nov., a new $H_2/CO_2$-utilizing acetogenlc bacterium isolated from human feces", Arch. Microbiol. (Sep. 1996) 166:176-183, Springer-Verlag 1996, New York, USA.
Bernalier, A., et al., "Diversity of $H_2/CO_2$-utilizing acetogenic Bacteria from Feces of Non-Methane-Producing Humans", Current Microbiology vol. 33 (Aug. 1996), pp. 94-99, Springer-Vertag New York Inc., USA.
Bond, John H., Jr., et al., "Factors Influencing Pulmonary Medicine Excretion in Man: An indirect method of studying the in situ metabolism of the methane-producing colonic bacteria"; Journal of Experimental Medicine, Oct. 29, 1970, pp. 572-388.
Born, P., et al., "Fecal bacterial activity in symptomatic carbohydrate malabsorption: Effect on the fecal short-chain fatty acid ratio", intervention during the week "Digestive Diseases Week" from May 16 to May 19, 1999, Orlando, Z. Gasteroenterol 2000: 38:623-626, Georg Thieme Verlag Stuttgart, New York, USA.
Born, P., et al., English Abstract "Carbohydrate substitutes: comparative study of intestinal absorption of fructose, sorbitol and xylitol", "Zuckeraustauschstoffe: Vergleichende Untersuchung zur intestinalen Resorption von Fructose, Sorbit und Xylit", Medizinische Klinik 89, Technischen Universitat Munchen (Munich) Nov. 15, 1994; 89 (11): 575-8 (Article in German), Urban & Vogel, Munich, Germany.
DMSZ: Opening of Ampoules and Rehydration of Dried Cultures; (http://web.archive.org/web/20000524115410/www.dsmz.de/open.htm); updated of website on Mar. 2000.
Durand, M., et al., "Reductive Acetogenesis in animal and human gut", Physiological and Clinical Aspects of Short-Chain Fatty Acids, (Jun. 1995), pp. 107-117.

(Continued)

*Primary Examiner*—Jon P Weber
*Assistant Examiner*—Kailash C Srivastava
(74) *Attorney, Agent, or Firm*—Arent Fox LLP

(57) ABSTRACT

The invention concerns the use of non-pathogenic hydrogenotrophic acetogenic bacterial strains for preparing a composition for treating or preventing gastrointestinal disorders associated with productions of digestive gases and/or for modulating the microbial balance of the digestive ecosystem in a mammal. The invention also concerns said pharmaceutical or food compositions, and the methods for monitoring and preparing said strains.

5 Claims, 2 Drawing Sheets

OTHER PUBLICATIONS

Gibson, Glenn R., "Dietary Modulation of the Human Gut Microflora Using the Prebiotics Oligofructose and Inulin", The Journal of Nutrition, 1999 American Society for Nutritional Sciences, pp. 1438S-1441S, USA.

Joblin, K.N., "Ruminal acetogens and their potential to lower ruminant methane emissions", Australian Journal of Agricultural Research, vol. 50, No. 8, pp. 1307-1313, Australia.

Keller, G.H. et al., "DNA Probes", 1994, Stockton Press, New York, 208660, USA.

King, T.S. et al., "Abnormal colonic fermentation in irritable bowel syndrome", The Lancet, vol. 352, Oct. 10, 1998, pp. 1187-1189, UK.

Nollet, L., et al., "Effect of the addition of *Peptostreptococcus productus*" ATCC35244 on the gastro-intestinal microbiota and its activity, as simulate in an in vitro simulator of the human gastro-intestinal tract, Appl. Microbiol. Biotechnol. (Jul. 1997) 48: 99-104, USA.

Pimentel, Mark, et al., "Methane Production During Lactulose Breath Test is Associated with Gastrointestinal Disease Presentation", Digestive Disease and Sciences, vol. 48. No. 1 (Jan. 2003), pp. 86-92, Plenum Publishing Corporation, New York, USA.

Rolfe, Rial D., et al., "The Role of Probiotic Cultures in the Control of Gastrointestinal Health ", Symposium: Probiotic Bacteria: Implications for Human Health, Experimental Biology, Symposium from Apr. 17 to Apr. 21, 1999, in Washington, DC, American Society for Nutritional Sciences 2000, pp. 396S-402S.

Schuler, et al., English abstract of and German article entitled "Physiologie und Pathologie des Intestinalflora Einfuhrung", last edition, beginning of the 1990's according to M. Angelo Schuler (on telephone on Jan. 12, 2007).

Van Nevel, C.J., et al., "Control of Rumen Methanogenesis", Environmental Monitoring and Assessment, vol. 42, 1996, pp. 73-97, Netherlands.

Liu, Chengxu et al., Reclassification of *Clostricium coccoides, Ruminococcus hanseniii, Ruminococcus hydrogenotrophicus, Ruminococcus luti, Ruminococcus productus* and *Ruminococcus schinkii* as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces, International Journal of Systematic and Evolutionary Microbiology (2008), 58, 1896-1902.

Bernalier, Annick et al., "Diversity of $H_2/CO_2$-Utilizing Acetogenic Bacteria from Feces of Non-Methane-Producing Humans"; Current Microbiology, vol. 33 (1996), pp. 94-99, Spring-Vertag New York Inc.

Joblin, K.N., "Ruminal acetogens and their potential to lower ruminant methane emissions"; Aust. J. Agric. Res., 1999, 50, 1307-1313, CSIRO, Australia.

Kamlage, Beate et al., "Isolation and Characterization of Two New Homoacetogenic Hydrogen-Utilizing Bacteria from the Human Intestinal Tract That Are Closely Related to *Clostridiuym coccoides*"; Applied and Environmental Microbiology, May 1997, vol. 63, pp. 1732-1738; American Society for Microbiology.

Lajoie, Steven F., et al., "Acetate Production from Hydrogen and [$^{13}$C]Carbon Dioxide by the Microflora of Human Feces"; Appl. Environ. Microbiol., vol. 54, 1988, pp. 2723-2727.

Rolfe, Rial D., "Symposium: Probiotic Bacteria: Implications for Human Health, The Role of Probiotic Cultures in the Control of Gastrointestinal Health"; as part of the Experimental Biology 99 meeting held Apr. 17-21 in Washington, D.C., American Society for Nutritional Sciences; pp. 396S-402S, 1999.

Wolin, Meyer J., et al., "Bacterial Strains from Human Feces That Reduce $CO_2$ to Acetic Acid"; Appl. Environ. Microbiol., Aug. 1993, pp. 3551-3556.

* cited by examiner

USE OF HYDROGENOTROPHIC ACETOGENIC STRAINS FOR PREVENTING OR TREATING DIGESTIVE DISORDERS

The invention relates to the use of nonpathogenic, hydrogenotrophic, acetogenic bacterial strains for preparing a composition for treating or preventing gastrointestinal disorders associated with digestive gas production, and/or for modulating the microbial balance of the digestive ecosystem in a mammal.

The prevalence of functional digestive disorders or functional gastrointestinal disorders in the Western population is very high since it is estimated that they affect approximately 25% to 30% of the adult population. In addition, these digestive disorders represent one of the main causes of consultation in gastroenterology (approximately 50% of consultations). The symptoms of these intestinal disorders are diverse, such as modification of intestinal transit, meteorism, abdominal pain and bloating. The cause of these functional disorders for the moment remains poorly defined, but it is estimated that the gases produced during digestion in the colon play an important role in generating certain symptoms such as flatulence excess, abdominal distension (bloating) and associated pain. Some treatments have been proposed, for instance active charcoal, simethicone, smectite, antispasmodics and also certain food supplements based on ferments (*Saccharomyces cerevisiae, Bifidobacterium, Lactobacillus*), on plants or on fiber (oligofructose, fennel, algae, oats, citrus fruits, etc.), or having a mineral structure (octalite, etc.). These treatments are, however, poorly effective on the symptoms linked to gas formation in the colon, and do not act selectively. The present invention proposes to remedy the drawbacks of the prior art, both in terms of treatment and in terms of preventing digestive discomfort associated with production of gas in the colon.

To do this, the invention is based both on the physiological characteristics of hydrogenotrophic acetogenic bacteria, namely their ability to reduce the total volume of digestive fermentation gases ($H_2$ and $CO_2$), and on their nutritional diversity which confers on them a considerable ecological advantage in the digestive ecosystem compared to other hydrogenotrophic microorganisms.

In humans, dietary carbohydrates which escape digestion and absorption in the small intestine arrive in the colon where they are fermented by a complex microflora. This anaerobic degradation of organic matter produces terminal metabolites in the form of volatile fatty acids having metabolic (acetate, propionate) or trophic (butyrate) properties and also gases ($H_2$, $CO_2$ and, in some individuals, $CH_4$).

Among these fermentation gases, $H_2$ plays an important role in the maintaining and the effectiveness of degradation of organic matter in the human colon. Some $H_2$ is eliminated via the respiratory and rectal pathways, but most of this gas is reutilized in situ by the intestinal flora. The latter, called hydrogenotrophic flora, is composed of acetogenic bacteria, of sulfur-reducing bacteria and of methanogenic archaea.

Sulfur-reducing bacteria are found in the digestive microflora of all individuals (Pochard et al. (1992) FEMS Microbiol. Lett. 98 p 225). They synthesize $H_2S$, which is a potentially toxic product for eukaryotic cells, and which is thought to be involved in some diseases of the digestive system, in particular ulcerative colitis (Roediger et al. (1993), Gastroenterology, 104, p 802).

Methanogenic archaea produce $CH_4$, which is a nontoxic gas. This methane production is only observed in a fraction of the human population (approximately 21% of adult Indians, 95% of the rural population of adolescents in black Africa and 40% of the Western population) and it is eliminated via the respiratory pathway and in flatulence (Segal et al. (1988) Gut 29 p 608; Pochart et al. (1992) FEMS Microbiol. Lett. 98 p 225). These individuals, called methane excreters, harbor a very large population of methanogenic archae ($>10^8$/g of dry fecal extract) (Durand et al. (1996) in: Mälkki Y and Cummings J H (eds Official Publications of the European Communities, p 58). In these individuals, methanogenesis is the main pathway for elimination of $H_2$.

Individuals who are not methane excreters re-use $H_2$ via alternative mechanisms, among which is reductive acetogenesis. This pathway constitutes a major metabolic process for using $H_2$ in non-methane excreters.

Studies have indeed shown that the fecal microflora of non-methane-excreting individuals mainly metabolizes $H_2$ and $CO_2$ to acetate, whereas that of methane-excreting individuals uses $H_2$ and $CO_2$ to form methane (Lajoie et al. (1988) Appl. Environ. Microbiol. 54 p 2733; Bernalier et al. (1996) FEMS Microbiol. Ecol. p 193). In parallel, Doré et al. (1995 FEMS Microbiol. Ecol. 17 p 279) have shown the existence of a negative correlation between the number of methanogenic archaea and that of acetogenic bacteria in the human colon. Non-methane-excreting individuals therefore harbor little or no methanogenic archaea in the colon, which would allow maximum expression of their acetogenic activity (Lajoie et al. (1988) Appl. Environ. Microbiol. 54 p 2733; Bernalier et al. (1996) FEMS Microbiol. Ecol. 19 p 193).

The hydrogenotrophic, acetogenic flora is characterized by great taxonomic diversity. It is composed of bacterial species belonging in particular to the *Clostridium, Ruminococcus* and *Streptococcus* genera (Bernalier et al. (1996) Curr. Microbiol. 33 p 94) and also of certain species of the *Eubacterium* genus (Schink (1994) in: Drake H L (ed) Acetogenesis. New York: Chapman and Hall p 197).

The term "hydrogenotrophic, acetogenic bacteria" is intended to mean bacterial species which use the reductive pathway for acetate synthesis (or Wood-Ljungdahl pathway) to produce this metabolite when they grow autotrophically using $H_2/CO_2$ and also when they grow heterotrophically using an organic substrate. These hydrogenotrophic, acetogenic bacteria have indeed a large nutritional capacity and, besides using $H_2/CO_2$, are capable of fermenting a considerable number of saccharides and of organic compounds (Bernalier et al (1996), Curr. Microbiol., 33 p 94).

The hydrogenotrophic, acetogenic bacterial strains according to the invention produce short-chain fatty acids (SCFA), in particular acetate, from $H_2$ and $CO_2$ gases. This production of SCFAs has a physiological advantage for the host, such as the prevention (protection) or treatment of diverse pathologies (see below).

The simultaneous presence of organic compounds and of $H_2/CO_2$ in the culture medium (conditions equivalent to those encountered in the human colon) may result in simultaneous use of the two substrates via the hydrogenotrophic, acetogenic strain (Breznak and Blum (1991), Arch. Microbiol., 156 p 105). This phenomenon, called mixotrophy, allows the bacterium to have a higher energetic yield and therefore to grow more rapidly.

This ability to consume $H_2/CO_2$ combined with the ability to use a large number of organic substrates and also the ability to grow by mixotrophy therefore confers a considerable ecological advantage on acetogenic bacteria compared to populations of methanogens which use only a limited number of substrates ($H_2$, formate), and sulfur-reducing populations which are dependent on the presence of sulfate for their $H_2$ metabolism.

It has been shown that the use of certain probiotic preparations, containing bacteria such as propionic bacteria, lactobacilli and/or bifidobacteria, makes it possible to modify the flora in the colon of certain patients (Bougle et al. (1999) Scand. J. Gastroenterol. 34 p 144; Venturi et al. (1999) Aliment. Pharmacol. Ther. 13 p 1103).

The use of acetogenic bacteria as probiotics as defined by Fuller (1989, J. Appl. Bact., 66 p 365), in preparations which can be used as food medicaments or as food supplements, therefore proves to be a particularly innovative pathway of interest, since their ability to metabolize $H_2/CO_2$ would make it possible to optimize fermentations in the colon by decreasing the total volume of fermentation gases and by producing acetate, a source of energy which can be metabolized by the host. The reduction of the digestive gases would thus be an effective means for preventing and/or treating digestive disorders associated with accumulation of these gases.

An object of the present invention is therefore the use of nonpathogenic, hydrogenotrophic, acetogenic strains, for regulating the abovementioned digestive disorders and/or modulating the balance of the microbial flora in a mammal.

The mammals according to the present invention are preferably monogastric mammals, as opposed to polygastric mammals such as ruminants. Felines and canines are particularly intended, especially domestic mammals (cats and dogs), and also humans.

The term "nonpathogenic" is intended to mean a microbial species for which no pathology of the host associated with its presence has been demonstrated (strain GRAS=Generally Recognized As Safe).

Such a use may be envisioned in various ways. The present invention relates to a prophylactic or therapeutic use, in order to prevent and/or treat certain disorders of the digestive system. This prevention and/or treatment may be carried out via regulation of the gases produced in the colon, through modulating the microbial flora. A use of this type may be envisioned under the direction of a physician or a health professional. In this case, the health professional decides upon the dose, the duration of treatment and also a possible combination of the nonpathogenic, hydrogenotrophic, acetogenic strain with other active principles effective in preventing and/or treating the digestive disorders targeted. Such a use may also require monitoring of the nonpathogenic, hydrogenotrophic, acetogenic strain using a method of analysis according to the invention, as defined later.

The present invention also relates to a therapeutic and/or prophylactic use in which the user, himself or herself, decides upon the administration of the nonpathogenic, hydrogenotrophic, acetogenic strain. The desired aim is then to decrease the discomfort of the user, who wishes, for example, to improve his or her quality of life.

Specifically, the digestive disorders targeted by the present invention affect the quality of life of the patients who suffer therefrom. The degree of digestive discomfort engendered and/or the capacity of each individual to put up with these disorders determine(s) whether or not affected individuals consult a physician.

In particular, the invention relates to the use of hydrogenotrophic, acetogenic strains, for preparing a composition for the following applications:

(1) preventing and/or treating digestive functional disorders,
(2) modulating the balance of the microbial flora in the colon by advantageously promoting the activity of the acetogenic bacterial flora, in particular to the detriment of the methanogenic and sulfur-reducing bacterial flora.

The latter point has the advantage:
(1) of decreasing the formation of $CH_4$ gas,
(2) of decreasing the production of $H_2S$, a toxic product, involved in initiating and/or developing digestive pathologies,
(3) of promoting the production of metabolites which are healthy for the host.

In particular, a strain of the *Ruminococcus, Clostridium* or *Streptococcus* genus, preferably *Ruminococcus hydrogenotrophicus*, is used.

Thus, the present invention relates to the use of at least one nonpathogenic, hydrogenotrophic, acetogenic bacterial strain, for preparing a composition for preventing and/or treating gastrointestinal disorders by reducing the formation of potentially toxic gases, and/or for modulating the microbial balance of the digestive ecosystem in a mammal. Such food or pharmaceutical compositions are also objects of the present invention.

Said reduction and/or said modulation is (are) carried out by decreasing the amount of gaseous hydrogen ($H_2$) and/or of gaseous carbon dioxide ($CO_2$) produced during digestive fermentations.

Said reduction and/or modulation may also be carried out by increasing the activity of the acetogenic flora in the colon to the detriment of the methanogenic and/or sulfate-reducing flora.

The gastrointestinal disorders that the use of a composition containing at least one hydrogenotrophic, acetogenic bacterial strain proposes to reduce are included in the group of functional gastrointestinal disorders, and in particular excessive flatulence, meteorism, bloating and abdominal pain, which are major criteria characterizing irritable bowel syndrome. The composition containing at least one hydrogenotrophic, acetogenic bacterial strain can also be used in the case of ulcerative colitis, of inflammatory bowel diseases or of Crohn's disease, in order to reduce the volume of gases in the colon, a factor which worsens the symptoms of these pathologies.

In a preferred embodiment of the invention, said composition is a food composition which can be used in the production of new foods or food ingredients as defined in EC Regulation No. 258/97, and in particular in the manufacture of functional foods. A food may be considered to be functional if it is demonstrated satisfactorily that it exerts a beneficial effect on one or more target functions in the organism, beyond the usual nutritional effects, improving the state of health and of well-being and/or reducing the risk of a disease (Diplock et al. Scientific concepts of functional foods in Europe: consensus document, British Journal of Nutrition, 1999, 81, S1-S27).

Said composition may in particular constitute a probiotic packaged, for example, in the form of a capsule or a gelatin capsule.

It is thus possible to use a food composition according to the invention which contains a nonpathogenic, hydrogenotrophic, acetogenic strain and which gives the user a feeling of well-being by reducing digestive discomfort.

In another preferred embodiment of the invention, said composition is a pharmaceutical composition, also combined with a pharmaceutically acceptable carrier, which may comprise excipients. It is preferably administered orally or directly in situ, in particular by coloscopy, or rectally via suppositories.

In another embodiment of the invention, the pharmaceutical composition also comprises at least one other agent active against at least one of the pathologies targeted.

The pharmaceutical or food composition according to the invention may be administered orally, in the form of gelatin capsules, of capsules, of tablets, of powders, of granules or of oral solutions or suspensions. The at least one bacterial strain can be mixed with conventional excipients, such as gelatin, starch, lactose, magnesium stearate, talc, gum arabic and the like. It may also be advantageous to use less conventional excipients, which make it possible to increase the ability of the at least one bacterial strain used to be active in the colon. For example, cellobiose, maltose, mannose, salicine, trehalose, amygdalin, arabinose, melobiose, rhamnose and/or xylose may be added. This list is not exhaustive and the substrates are chosen and adapted as a function of the strain considered. These substrates may promote heterotrophic and/or mixotrophic growth of the at least one acetogenic strain present in the composition.

Thus, the composition preferably comprises at least one additive which promotes the activity of the at least one strain in the digestive environment.

In a particular embodiment of the invention, the at least one nonpathogenic, hydrogenotrophic, acetogenic bacterial strain present in the pharmaceutical and/or food composition is administered in a form which allows it to be active in the colon. In particular, it is necessary for the at least one nonpathogenic, hydrogenotrophic, acetogenic bacterial strain to be alive, or viable, in the digestive tract, and in particular the colon. After production of the at least one nonpathogenic, hydrogenotrophic, acetogenic bacterial strain, and depending on the methods of production, it is also possible to maintain this strain under anaerobic packaging conditions in order to enable it to remain viable.

In a preferred embodiment, the at least one nonpathogenic, hydrogenotrophic, acetogenic bacterial strain is packaged in an anaerobic environment, i.e. it is packaged in an oxygen-free atmosphere.

In another preferred embodiment of the invention, the at least one nonpathogenic, hydrogenotrophic, acetogenic bacterial strain present in the composition is an autologous strain of said mammal, i.e. it can be isolated from the digestive system, in particular from the feces, of other mammals belonging to the same genus.

Preferably, and in particular when the mammal is a human, the at least one nonpathogenic, hydrogenotrophic, acetogenic bacterial strain belongs to the *Ruminococcus* genus, even more preferably to the species *Ruminococcus hydrogenotrophicus*. Other hydrogenotrophic, acetogenic bacteria, in particular bacteria of the *Streptococcus* or *Clostridium* genus, in particular *Clostridium coccoides*, can also be used.

The invention also relates to a method for specifically monitoring the nonpathogenic, hydrogenotrophic, acetogenic bacterial strain in the digestive tract of a mammal, after it has been used as defined above, comprising the following steps:
  a. a nucleotide sequence (probe) specific for the nonpathogenic, hydrogenotrophic, acetogenic strain the detection of which is desired is defined;
  b. said strain is detected and/or quantified by hybridization of the probe with total nucleic acid extracted from the fecal flora, or with the fecal bacteria attached to a slide.

In order to carry out such a monitoring method, diagnostic kits, which are also objects of the present invention, can be developed. Such kits contain in particular a "standard" in order to be able to evaluate the amount of bacteria in the feces.

Those skilled in the art are capable of defining a specific sequence which does not hybridize with the DNA of other bacteria. Similarly, those skilled in the art will choose hybridization on a membrane or in situ hybridization depending on the means available to them, and on the desired precision.

Preferably, the nucleic acid detected is the total bacterial DNA, but can also be a mixture of DNA or of RNA, or the bacterial RNA alone.

The presence of the at least one nonpathogenic, hydrogenotrophic, acetogenic bacterial strain can also be studied using other methods. Detection of the nucleic acids (DNA and/or RNA) of the at least one nonpathogenic, hydrogenotrophic, acetogenic bacterial strain in the feces of the mammal, in particular by PCR or RT-PCR or by hybridization with specific probes (Southern or Northern) will make it possible to detect the presence of said strain and, optionally, the expression of certain genes. An advantageous specific sequence can be chosen in the sequence of the gene encoding the 16S rRNA, in particular a region which is not present on the other species of the flora in the colon.

The invention also covers a method for producing a nonpathogenic, hydrogenotrophic, acetogenic bacterial strain, for its use as defined above, characterized in that it comprises the following steps:
  a. the strain is grown on a suitable medium, under conditions of strict anaerobiosis, in the presence of a carbon-based substrate and/or of $H_2/CO_2$ as energy source;
  b. the bacterial cells are recovered;
  c. the bacterial cells are packaged according to the pharmaceutical form chosen.

The strain will preferably be grown in a modified AC21 medium (described in example 1), at 37° C., in a fermenter. The carbon-based substrate may be glucose.

A preferred method for recovering the bacterial cells is centrifugation, for example between 10 000 g and 15 000 g, advantageously 12 000 g, for 15 to 20 minutes. Those skilled in the art are capable of optimizing these parameters.

The bacteria may advantageously be washed between steps b and c, in particular in an anaerobic phosphate buffer, by resuspension of the cells, agitation, and a further centrifugation step.

The bacterial pellet, which may or may not be washed, is packaged as a function of the pharmaceutical form chosen. An advantageous method is lyophilization.

The following examples make it possible to illustrate the invention but should not, however, be considered to be limiting.

EXAMPLES

Example 1

Isolation of the Microorganisms

Figure 1:
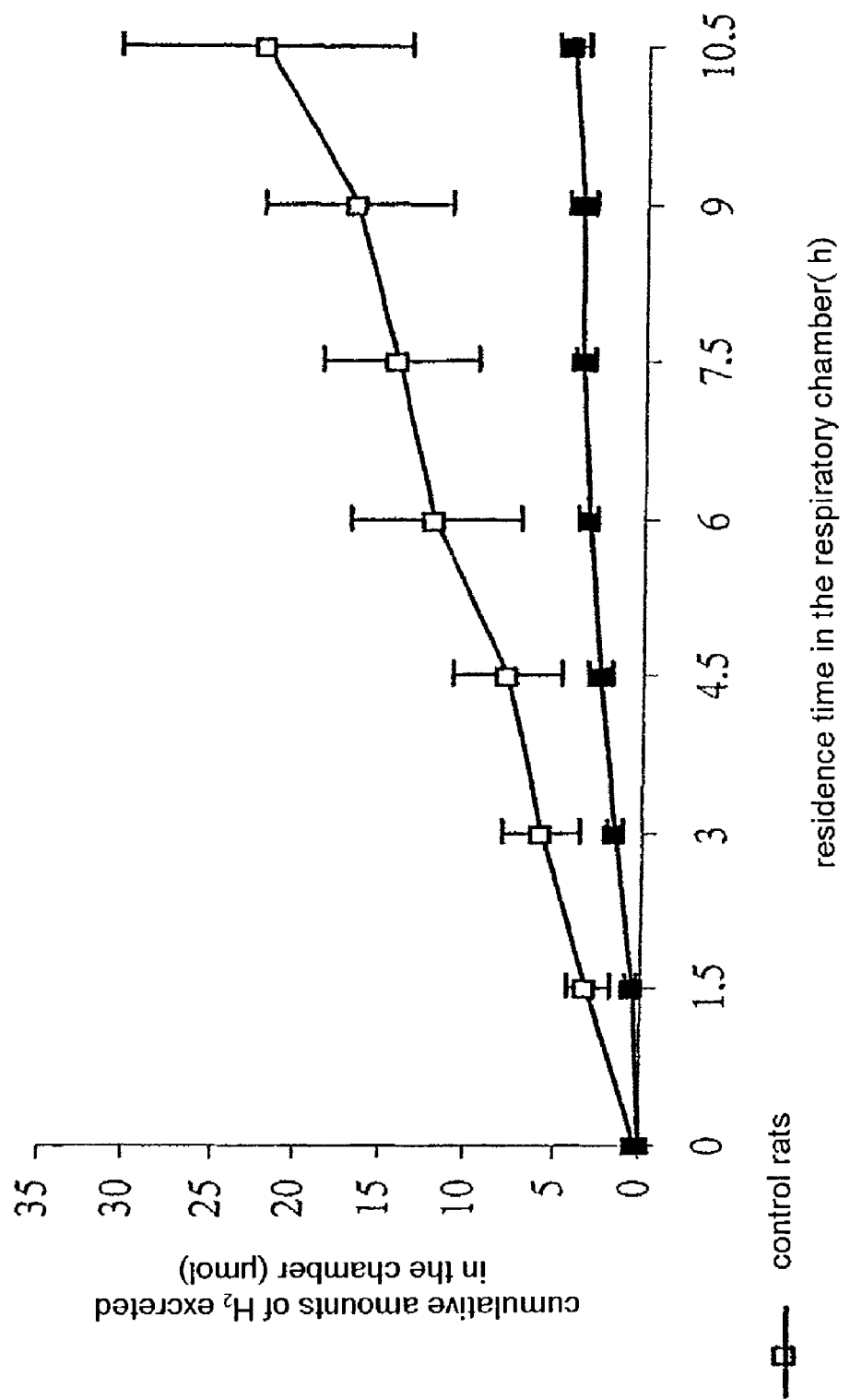
FIG. 1: Influence of a 14-day treatment with *Ruminococcus hydrogenotrophicus* on the amounts of hydrogen excreted by rats with human flora in a normal nutritional situation.

Human fecal samples from healthy non-methane-excreting volunteers are used. Individuals are considered to be non-methane-excreting when their level of expired methane does not exceed by more than 1 ppm that of ambient air, which is 1.8 ppm (Bond et al. (1970) Gastroenterology 58 p 1035), and when the number of methanogens contained in their fecal extracts is less than $10^7$/g of fecal extract (Bernalier et al.

(1996) Arch Microbiol. 166 p 176). The level of methane is determined using a chromatograph equipped with a flame ionization detector. The freshly taken fecal samples are kept at 4° C. under strict anaerobiosis for a maximum of 10 hours.

The enriching, isolating and culturing of the microorganisms are carried out on a semi-synthetic medium, modified AC-21 medium (Breznak et al. (1988) Arch. Microbiol. 150 p 282) under strict anaerobiosis (Hungate (1969) in: Norris J R and Gibbons D W (eds) Methods in microbiology Vol. 3B, New York: Academic Press p 117). The composition per liter of the semi-synthetic medium is as follows:

| | |
|---|---|
| $KH_2PO_4$ | 0.2 g |
| $NH_4Cl$ | 0.25 g |
| KCl | 0.5 g |
| $CaCl_2 \cdot 2H_2O$ | 0.15 g |
| $MgCl_2 \cdot 6H_2O$ | 0.6 g |
| $Na_2SO_4$ | 0.1 q |
| Yeast extract | 0.5 g |
| Tryptone | 2 g |
| Trace element solution | 1 ml |
| Tungstate-selenium solution | 0.1 ml |
| Vitamin solution | 5 ml |
| Resazurin solution (1%, w/v) | 1 ml |
| $NaHCO_3$ (1 M) | 30 ml |
| Cysteine/sulfide reductive solution (1.25%/1.25%, w/v) | 20 ml |

The trace element solution is prepared according to Widdel et al. (1983, Arch. Microbiol., 134, p 286), and the vitamin solution is prepared according to Greening and Leedle (1989, Arch. Microbiol., 151, p 399). The tungstate-selenium solution has the following composition: 0.1 mM $Na_2WO_4$ and 0.1 mM $Na_2SeO_3$, in 20 mM NaOH.

The semi-synthetic medium is solidified by adding a gelling agent (agar at 2%). After inoculation, the gas of the culture medium is replaced with $H_2/CO_2$ or $N_2/CO_2$ depending on the test envisioned.

The dilution medium is a purely inorganic anaerobic medium (Doré et al. (1995) FEMS Microbiol. Lett. 130 p 7). A stock solution is prepared (diluted to one tenth, w/v) from a fecal sample. A series of ten-fold dilutions is prepared from the stock suspension. The dilutions thus prepared are inoculated into the semi-synthetic liquid medium containing $H_2/CO_2$ (60:40, v/v, 202 kPa) as the only energy source (Doré et al. (1995) FEMS Microbiol. Lett. 130 p 7; Bernalier et al. (1996) FEMS Microbiol. Ecol. 19 p 193; Bernalier et al. (1996) Curr. Microbiol. 33 p 94). After incubation at 37° C. for 20 days, the enrichments are obtained from the highest dilution tubes exhibiting the highest bacterial growth, gas consumption and stoichiometric production of acetate (Bernalier et al. (1996) Curr. Microbiol. 33 p 94). The decrease in gas pressure in the cultures is determined by directly measuring partial pressure with a manometer of the Capsuhelic type (Dwyer, Instruments, Michigan City, Mich., USA). After three transfers of the enriched cultures, bacterial colonies are isolated using the method of roll-tubes (Hungate (1969) in: Norris J R and Gibbons D W (eds) Methods in microbiology Vol. 3B, New York: Academic Press p 117) containing a homologous agar medium and $H_2/CO_2$ as energy source. After incubation for 20 days at 39° C., the colonies are transferred into liquid media. Purification of the cultures is obtained after 3 to 5 successive transfers in roll-tubes, at the end of which the purity of the cultures is determined by phase-contrast microscopy, after Gram staining.

The total DNA of the isolated hydrogenotrophic, acetogenic strains is extracted by the method of Lawson et al. (1989, FEMS Microbiol. Lett. 65 p 41). The gene encoding the 16S ribosomal RNA is then amplified by PCR using the universal primers ARI and pH. The PCR products are purified and then sequenced using a "Dye-Dideoxy Terminator cycle Sequence" kit and an Applied Biosystem model 373A automatic sequencer. The search for 16S rRNA sequence homology between the isolated acetogenic strains and the other species is carried out using the FASTA program, the sequence databases being those of EMBL and of RDP, and using the suggested basic parameters. The sequence alignments are verified manually.

Using this method, it was possible to isolate a bacterium of the *Ruminococcus* genus, identified as being the species *Ruminococcus hydrogenotrophicus*. This bacterium was deposited with the Deutsche Sammlung von Mikroorganismen [German Microorganism Collection] (Mascheroder Weg 1b, 38124 Braunschweig, Germany) under the number DSM 10507, and also under the number DSM 14294, on May 10, 2001 (Treaty of Budapest).

Example 2

Study of the General Characteristics

1—The membrane type of the bacteria is determined by Gram staining (conventional method) and by the KOH test according to Buck (1982 App. Environ. Microbiol. 44 p 992).

2—The catalase activity is measured by mixing 1 ml of bacterial suspension with a few drops of $H_2O_2$ (30%). The production of gas bubbles being released more or less strongly indicates the presence of a catalase.

3—The cytochrome oxidase activity is studied by placing a bacterial colony on a disk of filter paper saturated with dimethyl p-phenylenediamine. A red/purple coloration occurring immediately on the disk indicates that the test is positive.

4—The morphological characteristics of the cultures are studied by phase-contrast microscopy and by electron microscopy after negative staining with 2% uranyl acetate. The cells are pre-fixed in 2% glutaraldehyde (15 h at 4° C.) and then fixed with 2% $OsO_4$ (4° C., for a maximum of 15 h). The cells are then embedded in EPPON-812 and the blocks are very thinly sectioned. These sections are contrasted with uranyl acetate, soaked in acetate salt and observed with a transmission electron microscope (Philips 400).

5—The respiratory type of the bacteria is studied by determining growth in the presence or absence of $O_2$.

6—The effect of variations in pH on bacterial growth is studied by modifying the $CO_2/NaHCO_3$ ratio of the semi-synthetic medium (Costilow (1981) American Society for Microbiology, Washington D.C. p 66). The bacterial growth is measured (DO600) after 24 or 48 h of incubation at 37° C. Investigation of the optimal growth temperature is carried out on semi-synthetic medium containing glucose and the growth is observed at temperatures ranging from 20 to 45° C. Each experiment is carried out in triplicate. Bacterial growth is monitored using a Spectronic 20D spectrophotometer (Bioblock Scientific, Illkirch, France).

It was found that *Ruminococcus hydrogenotrophicus* DSM 10507 is an unsporulated, strictly anaerobic Gram-positive coccobacillus. The negative staining reveals the absence of flagellae. The bacterial cells are individual or in pairs. The strain does not have catalase or cytochrome oxidase. The optimal growth temperature and pH are, respectively, 35-37° C. and 6.6. The colonies are translucent, white to slightly brown in color with regular edges, circular and between 1 and 2 mm in diameter.

Example 3

Growth Test, Determination of the Acetogenic Activities

The ability of various bacterial strains to metabolize $H_2/CO_2$ and to form acetate is studied. The strains of *Ruminococcus hydrogenotrophicus* DSM 10507, and also those taxonomically close, *Ruminococcus productus* DSM 3507, *Ruminococcus productus* DSM 2950, *Ruminococcus hansenii* DSM 20583 and *Clostridium coccoides* DSM 935 (DSM numbers corresponding to the numbers of the organisms deposited with the Deutsche Sammlung von Mikroorganismen), are incubated on the modified AC-21 medium in the presence of $H_2/CO_2$ (60:40, v/v, 202 kPa) as energy source. Control cultures are incubated under $N_2/CO_2$ (60:40, v/v, 150 kPa). Three cultures (1 control and 2 tests) are prepared for each bacterial strain. The autotrophic growth is determined by incubation for 96 h in the presence of $H_2/CO_2$ (60:40, v/v, 202 kPa). Acetate production is measured using an enzymatic test (Boehringer Mannheim, Meylan, France), after incubation for 6 days at 37° C.

$H_2/CO_2$ consumption is measured by determination of the gaseous volume consumed by chromatographic (CPG) analysis of the composition of the gaseous phase.

The heterotrophic growth of the acetogenic strains ($OD_{600}$) is studied by incubating the bacteria for 20 h with glucose (2 g/l) or fructose (2 g/l) as the only source of energy.

The glucose fermentation is studied by incubating the cells at 37° C. for 20 h on the semi-synthetic medium containing 2 g/l of glucose and an atmosphere composed of 100% of $CO_2$. At the end of incubation, the volatile fatty acids of the supernatant are assayed by chromatography, after conversion to tertiary derivatives of butyldimethyl (Richardson et al. (1989) Lett. Appl. Microbiol. 9 p 5).

It is observed that the doubling time for *R. hydrogenotrophicus* at 37° C. on modified AC-21 medium in the presence of $H_2/CO_2$ (60:40, v/v, 202 kPa) as substrate is 26.4 h. The doubling times for *R. hydrogenotrophicus* at 37° C. with glucose or fructose as energy source are approximately 2 or 3 h.

It is observed that the bacterial strain studied is acetogenic: it exhibits autotrophic growth in the presence of $H_2/CO_2$ and produces acetate as major metabolite (Table I). Among the taxonomically close species, acetogenic activity (i.e. consumption of $H_2/CO_2$ and production of acetate) is found in *C. coccoides* and much more weakly in *R. hansenii* and *R. productus*.

*R. hydrogenotrophicus* DM 10507 consumes approximately 120 mM of $H_2$ after 96 hours of culturing at 37° C. (1.25 mM of $H_2$ consumed per hour). Total acetate production is then equal to 30 mM (stoichiometry: $4H_2$ consumed per acetate formed).

TABLE I

Fermentation characteristics of the strains cultured in the presence of $H_2/CO_2$ or glucose as the only energy source.

| Properties | *R. hydrogenotrophicus* DSM 10507 | *C. coccoides* DSM 935 | *R. productus* DSM 3507 | *R. productus* DSM 2950 | *R. hansenii* DSM 20853 |
|---|---|---|---|---|---|
| Use of $H_2/CO_2$ | ++ | + | – | + | +/– |
| $H_2/CO_2$ FP | | | | | |
| Acetate | ++ | + | – | + | +/– |
| Propionate | – | – | – | – | – |
| Butyrate | – | – | – | – | – |
| Lactate | – | – | – | – | – |
| Succinate | – | – | – | – | – |
| Ethanol | – | – | – | – | – |
| Glucose FP | | | | | |
| Acetate | ++ | + | ++ | ++ | ++ |
| Propionate | – | – | – | – | – |
| Butyrate | – | – | – | – | – |
| Lactate | + | – | – | – | + |
| Succinate | – | ++ | – | – | + |
| Ethanol | + | – | + | + | – |

Symbols:
FP: fermentation products; ++, major metabolite; +, nonmajor metabolite; +/–, metabolite produced in small amount; –, metabolite not produced.

Example 4

Estimation of the Hydrogenotrophic, Acetogenic Capacity of *R. hydrogenotrophicus* by Measurement of the Incorporation of $^{13}CO_2$ into Acetate (NMR Method)

The incorporation of $^{13}CO_2$ into acetate is measured by NMR using cell suspensions of *R. hydrogenotrophicus* incubated in the presence of $H_2$. The bacteria are cultured in a 1 l flask containing 250 ml of AC21 medium as described in example 1, and $H_2/CO_2$ as the only energy source. After growth at 37° C., the bacterial cells are recovered by centrifugation (12 000 g for 20 minutes) and resuspended in a phosphate buffer containing 20 mM of $NaH^{13}CO_3$ (Leclerc et al (1997), Anaerobe, 3, p 307). The suspensions are incubated for 20 hours at 37° C., under an atmosphere composed of 100% of $N_2$ (control) or of $H_2/N_2$ (80/20, v/v), at 101 atm. At the end of incubation, the suspensions are again centrifuged at 12 000 g for 20 minutes and the supernatants are recovered. Total acetate production is measured by an enzymatic method (Boehringer-Mannheim kit). The $^{13}C$-labeled metabolites are analyzed by NMR (Bernalier et al, (1996), FEMS Microbiol. Ecol., 19, p 193).

When the bacterium is incubated in the presence of $H_2$, the only metabolite detected by $^{13}C$ NMR is acetate. The $^{13}C$-acetate is labeled in an equivalent manner on its methyl and carboxyl groups. The double-labeled acetate represents 72% of the total labeled acetate. This confirms that the synthesis of acetate from $H_2$ and $CO_2$ by *R. hydrogenotrophicus* occurs via the reductive pathway for acetogenesis.

Example 5

Determination of the Nutritional Capacities of the Acetogenic Bacteria

The metabolism of other organic substrates by the acetogenic bacteria is evaluated using a modified AC-21 medium containing 5 or 10 mM of substrate, in an atmosphere composed of 100% $CO_2$. The test is considered to be positive when the bacterium maintains its growth after three successive transfers on a medium containing the same substrate, and if the $OD_{600}$ of the culture is at least equal to double that observed with a basal semi-synthetic medium (free of organic substrate), after incubation for 24 h at 37° C.

It is observed that many organic substrates allow heterotrophic growth of the bacteria considered (Table II).

TABLE II

Growth of *R. hydrogenotrophicus* and of the taxonomically close species in the presence of various organic substrates

| Substrate | R. hydrogenotrophicus DSM 10507 | C. coccoides DSM 935 | R. productus DSM 3507 | R. productus DSM 2950 | R. hansenii DSM 20853 |
|---|---|---|---|---|---|
| Starch | − | − | + | + | − |
| Amygdalin | − | + | + | + | +/− |
| Arabinose | − | + | + | + | − |
| Cellobiose | + | + | + | + | − |
| Fructose | + | + | + | + | − |
| Galactose | + | + | + | + | + |
| Inulin | − | − | − | − | + |
| Lactose | + | + | + | + | + |
| Maltose | +/− | + | + | + | + |
| Mannitol | − | + | + | + | − |
| Mannose | + | + | + | + | − |
| Melibiose | +/− | + | + | + | + |
| Raffinose | + | + | + | + | + |
| Rhamnose | − | + | − | − | − |
| Salicine | + | + | + | + | − |
| Sorbitol | − | + | + | + | − |
| Sucrose | − | + | + | + | − |
| Trehalose | + | + | + | + | + |
| Xylose | − | + | + | + | − |

Symbols:
−, no visible growth; +/−, weak growth; +, good growth.

Furthermore, the growth of various hydrogenotrophic, acetogenic strains isolated from human stools, in the presence of various aromatic compounds such as vanillate, caffeate or syringate, is estimated by measuring the optical density at 600 nm using a Spectronic 20D spectrophotometer (the effect of adding $H_2$ to the gaseous phase of these cultures is also studied). The amount of degraded substrate is determined by HPLC, as is the nature of the metabolites formed.

The ability to metabolize the various aromatic substrates tested depends on the hydrogenotrophic, acetogenic strain considered. The *Clostridium* species are capable of growing and of degrading 20% to 30% of the caffeate and of the syringate, this degradation reaching 100% when $H_2$ is added to the culture. One of the strains of *Clostridium* degrades vanillate only in the presence of $H_2$ in the gaseous phase. This strain demethylates the vanillate to protocatechuate in a first step, and then, using $H_2$, decarboxylates this compound to catechol. The *R. hydrogenotrophicus* strain exhibits only weak activity with respect to vanillate, this metabolism not appearing to be influenced by the presence of $H_2$.

The ability of *R. hydrogenotrophicus* to use 2 organic substrates not able to be digested by the host's enzymes, fructo-oligosaccharides (FOS) and lactulose, is also determined according to the protocol described in this example [measurement of bacterial growth (optical density at 600 nm) observed in the presence of 2 g/l of each of the indigestible substrates, and maintenance of this growth after 3 successive transfers on the same substrate]. *R. hydrogenotrophicus* proves to be incapable of metabolizing these 2 substrates.

Example 6

Mixotrophic Nature of the Hydrogenotrophic, Acetogenic Strain Ruminococcus Hydrogenotrophicus In order to determine whether *R. hydrogenotrophicus* is capable of growing by mixotrophy (simultaneous use of an organic substrate and of an inorganic substrate), the strain is cultured in the presence of two energy sources, one organic, glucose, and the other inorganic, $H_2/CO_2$. The culture medium (modified AC21 medium as described in example 1) contains 1.4 mM of glucose and the gaseous phase is replaced, after seeding, with a mixture of $H_2/CO_2$ (60/40 at 156 kPa). The cultures are inoculated with 0.3 ml of a preculture of *R. hydrogenotrophicus* obtained either with glucose or with $H_2/CO_2$ as the only energy source. The consumption of gas by the strain is monitored during the incubation at 37° C., using pressure sensors attached to the culture stoppers (Leclerc et al. (1997), Anaerobe 3 p 307). Bacterial growth is estimated by measuring the optical density of the cultures at 600 nm using a Spectronic 20D spectrophotometer. Culture supernatant samples are taken every 2 hours in order to estimate glucose consumption (assay of remaining glucose using Boehringer enzymatic method) and fermentative metabolite production by chromatographic assaying (as described in example 3).

*R. hydrogenotrophicus* proves to be capable of co-using the two substrates tested. A single exponential growth phase for the bacterium is observed in the presence of the two substrates. During this exponential phase, simultaneous consumption of glucose and of $H_2/CO_2$ is observed. This reflects the mixotrophic nature of *R. hydrogenotrophicus* with regard to these 2 substrates (Leclerc and Bernalier, submitted for publication). At the end of the exponential phase, the glucose has been completely consumed by the bacterium, which bacterium then maintains its metabolism in the stationary growth phase by using the remaining $H_2/CO_2$.

The ability of *R. hydrogenotrophicus* to cometabolize a sweetener, fructose, and $H_2/CO_2$, is also studied. The strain is cultured on the AC21 medium, as described in example 1, in the presence of these two energy sources. Various concentrations of fructose are tested (2, 1, 0.5 and 0.25 g/l), the gaseous phase still being composed of $H_2/CO_2$ (60/40, v/v, 202 kPa). The experimental protocol then used is the same as that described above.

*R. hydrogenotrophicus* proves to be capable of cometabolizing fructose and $H_2/CO_2$, the bacterial growth being characterized by a single exponential growth phase in the presence of the two substrates. This mixotrophic growth is observed whatever the concentration of fructose present in the culture medium and whatever the origin of the bacterial inoculum (preculture prepared on fructose or $H_2/CO_2$ or fructose+$H_2CO_2$). In the stationary growth phase, the bacterium metabolizes only $H_2/CO_2$, all the fructose having been consumed.

Example 7

Effect of Lyophilizing the *Ruminococcus hydrogenotrophicus* Cultures on Expression of the Hydrogenotrophic Activity In order to determine whether conserving *R. hydrogenotrophicus* in lyophilized form may impair its ability to use $H_2/CO_2$, various conditions for culturing, for conserving the lyophilizates, and for resuspending the bacterium are tested.

*R. hydrogenotrophicus* cultures are prepared in 1 l flasks containing 250 ml of AC21 medium as described in example 1, with fructose (2 g/l), $H_2/CO_2$ (60/40, v/v, 100 kPa) or both substrates as energy source. These cultures are incubated at 37° C. for 24 h, 48 h or 72 h, depending on the substrate(s) used. Bacterial pellets are then obtained by centrifugation (15 300×g, 30 min, 4° C.) of the cultures and are taken up in 10 ml of anaerobic buffer. The suspensions thus obtained are aliquoted by 2 ml and then centrifuged for 5 min at 14 000×g. The bacterial pellets are then frozen at −80° C. before being lyophilized overnight. The lyophilizates are stored at 4° C. under an aerobic or anaerobic (100% of $CO_2$) atmosphere. After storage for 15 to 30 days, the *R. hydrogenotrophicus* lyophilizates are taken up in 5 ml of anaerobic dilution buffer. These bacterial suspensions are then seeded into an AC21 medium containing $H_2/CO_2$ (60/40, v/v, 200 kPa) as the only energy source either directly or after enrichment for 48 h at 37° C., in a complex culture medium containing various carbon sources. After incubation for 72 h at 37° C. in the presence of $H_2/CO_2$, the consumption of $H_2$ and the amount of acetate produced are determined for each culture.

Lyophilization of *R. hydrogenotrophicus* does not appear to affect its hydrogenotrophic potential. The reason for this is that, whatever the substrate used to preculture the strain (fructose, $H_2/CO_2$ or both substrates simultaneously), the hydrogenotrophic activity of *R. hydrogenotrophicus* is restored when the lyophilizates are placed in culture. Similarly, the aerobic or anaerobic method of storing the lyophilizate has little influence on the expression of the hydrogenotrophic potential of the bacterium. However, maximum hydrogenotrophic activity is observed when *R. hydrogenotrophicus* is precultured in the presence of fructose and when the lyophilizate is stored under an anaerobic atmosphere. Similarly, prior culturing of the lyophilized bacteria on a medium rich in organic substrates substantially increases the expression of their hydrogenotrophic potential, whatever the substrate used to preculture the strain and whatever the method of storage of the lyophilizate. This effect is probably explained by the increase in bacterial density engendered by the enrichment of the lyophilized cultures on complex medium.

All the results obtained demonstrate that the *R. hydrogenotrophicus* strain can be cultured in the presence of organic substrate and then stored at 4° C. in lyophilized form in an aerobic or anaerobic atmosphere, without this substantially affecting the subsequent expression of its hydrogenotrophic potential.

Example 8

Interspecies Transfer of $H_2$, in vitro, Between $H_2$-Producing Fibrolytic Bacteria and *R. hydrogenotrophicus*

The ability of *R. hydrogenotrophicus* to use the $H_2$ produced by fibrolytic bacterial species is studied in vitro, in cocultures combining the acetogenic strain with a cellulolytic bacterium. The two cellulolytic species studied were isolated in the laboratory from human stools. The cocultures are prepared on a semi-synthetic medium, developed in the laboratory, containing a small cellulose strip of Whatman No. 1 filter paper as the only carbon and energy source. Each one of these cellulolytic species is seeded in a proportion of 0.5 ml of inoculum per culture tube. After incubation for 48 h at 37° C., 0.5 ml of *R. hydrogenotrophicus* inoculum is added to each one of these cultures of cellulolytic bacteria. Control monocultures of each cellulolytic species are prepared in parallel.

Kinetics are produced by incubating the cultures at 37° C. for 12 days. After incubation, the amount of $H_2$ in the gaseous phase is analyzed by chromatography, the amount of cellulose degraded is estimated by measuring the remaining solids and the final products of fermentation of the cellulose are determined by gas phase chromatography and/or by enzymatic pathways (Roche kit).

The addition of *R. hydrogenotrophicus* to one or other of the $H_2$-producing cellulolytic species results in a large decrease in this gas in the cocultures, whereas it accumulates in the gaseous phase of the monocultures.

*R. hydrogenotrophicus* is therefore capable of effectively re-using the $H_2$ produced in vitro by a fibrolytic species during fermentation of cellulose. This transfer of $H_2$ between *R. hydrogenotrophicus* and the cellulolytic species causes only slight or no modification of the cellulolytic activity of the fibrolytic species studied. On the other hand, the cellulose is mainly fermented to acetate in the cocultures, whereas it is rather of the mixed-acid type in the monocultures (production of acetate, of succinate or of ethanol and of lactate).

Example 9

Ability of the Hydrogenotrophic, Acetogenic Strain *Ruminococcus hydrogenotrophicus* to Reduce the Volume of Gases in the Colon In Vivo, in Rats with Human Flora In order to determine whether *R. hydrogenotrophicus* is capable of reducing the volume of gases in the colon in the presence of a complex digestive flora, *R. hydrogenotrophicus* is administered orally to rats with human flora and the change in the volume of gas in the colon is monitored by measuring the hydrogen excreted via the respiratory and rectal pathways.

The effect of *R. hydrogenotrophicus* is studied in a normal nutritional situation and after administration of a fermentable substrate (lactulose) causing an abrupt increase in the volume of gas in the colon.

The animals used are male Fischer 344 rats, 3 months old at the beginning of the experiment. They are born free of microorganisms, and are inoculated per os with 1 ml of a centesimal suspension of fresh human fecal matter from a nonmethanogenic adult donor having a Western-type diet. The inoculation takes place 2 weeks before the beginning of the experiment. The rats are housed in isolators and receive a semi-synthetic "human-type" feed (proteins and fats of animal and plant origins; raw and cooked, simple and complex carbohydrates), sterilized by γ-irradiation at 45 kGy. Food and drinking water are distributed ad libitum.

Normal Nutritional Situation

The experiment is carried out with 16 rats with human flora, divided into 2 groups of 8, a control group and a treated group. The rats in the treated group receive, each morning for 28 days, by gastric intubation, a dose of $10^8$ to $10^9$ bacteria in the form of 1 ml of an *R. hydrogenotrophicus* culture cultured for 18 h on AC21 medium (as described in example 1) containing glucose (2 g/l). The control group receives, under the same conditions, 1 ml of sterile AC21 medium containing glucose.

After 1, 14 and 28 days of treatment, the rats in the 2 groups are placed in individual respiratory chambers for 12 h, making it possible to measure the hydrogen excreted via the respiratory and rectal pathways (see description of the respiratory chambers below). Air samples are taken in duplicate from the respiratory chambers between 0 h and 12 h. The hydrogen concentration is immediately determined by gas phase chromatography. The results of the control and treated groups are compared using an ANOVA for repeated measurements.

Whatever its duration of treatment, the administration of *R. hydrogenotrophicus* significantly decreases the maximum amount of hydrogen excreted (−50% to −80%) and the excretion rate (−60% to −80%) compared to the control group (P<0.01). The treatment proves to be as effective after 1, 14 or 28 days (FIG. 1).

The hydrogenotrophic, acetogenic flora is counted (Doré et al, 1995) in the feces of the rats of the two groups, at various times during the experiment. In the control group which does not receive *R. hydrogenotrophicus*, the level of the acetogenic population is stable over time and comparable to that of the donor, i.e. approximately log 6.8 acetogens per g of feces.

The treatment with *R. hydrogenotrophicus* leads to an increase in the level of acetogenic flora, which then reaches log 7.5/g of feces from 24 h of treatment. This level is maintained until the end of the experiment. The increase in acetogenic flora in the treated rats therefore coincides with the decrease in the amounts of $H_2$ excreted by these animals.

At the end of the experiment, the rats are sacrificed by euthanasia and autopsied. The administration of *R. hydrogenotrophicus* has no significant effect on either the bodyweight or the weight of the liver, the kidneys and the cecum, or on the pH of the cecum (P>0.05). Similarly, the macroscopic appearance of the liver and of the kidneys of the rats treated with *R. hydrogenotrophicus* is normal and identical to that of the control rats.

b) After Administration of Lactulose

This experiment is carried out according to the same protocol as above. Lactulose (4-O-β-D-galactopyranosyl-D-fructose), the fermentation of which in the colon leads to an abrupt increase in the volume of gas, is administered by gastric intubation, in a proportion of 500 mg per rat, just before they are placed in respiratory chambers. The effect of *R. hydrogenotrophicus* on this increase is examined after 1 and 14 days of treatment with the acetogenic strain.

Figure 2:
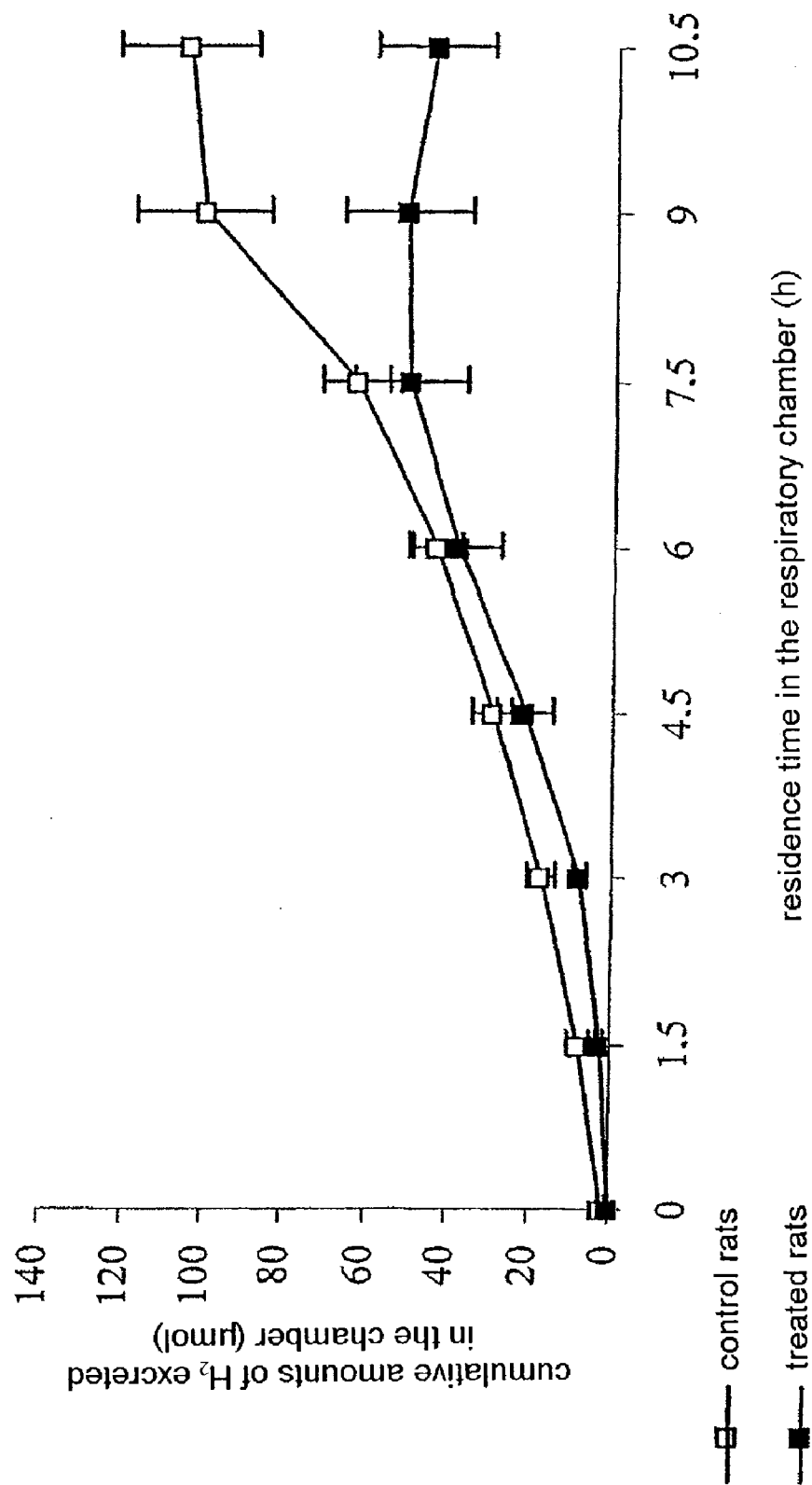
FIG. 2: Influence of a 14-day treatment with *Ruminococcus hydrogenotrophicus* on the amounts of hydrogen excreted by rats with human flora after administration of lactulose.

Under these conditions of excessive production of gases in the colon, the administration of *R. hydrogenotrophicus* significantly decreases the maximum amount of hydrogen excreted (−40% to −50%) and the excretion rate (−40% to −50%) compared to the control group (P<0.05). The treatment proves to be as effective after 1 or 14 days (FIG. 2).

In the 2 experiments, the rats treated with *R. hydrogenotrophicus* showed no behavioral abnormality and the appearance and consistency of the feces was identical to those of the control rats.

The respiratory chambers used are sealed autonomous chambers made of transparent rigid polyvinyl, with a volume of 30 liters, making it possible to house a cage containing a small animal. They are equipped with a double door for sealed transfer, making it possible to connect them to the experimental isolators.

In order to preserve the bacterial status of the animals, they are sterilized before being connected. After transfer of the animal from the isolator to the respiratory chamber, the latter is detached from the isolator and connected to a closed circuit in which the air is pushed, using a peristaltic pump, through antibacterial filters and systems for removing the $CO_2$ (absorber containing a solution of potassium hydroxide at 40%) and the water vapor (absorber containing silicagel crystals). The $O_2$ content in the air is measured with a sensor and kept constant at 21% using an amperometric electrode, a control unit and a solenoid valve.

This device allows accumulation of the gases specific for fermentations in the colon (hydrogen and, where appropriate, methane), excreted via the respiratory and rectal pathways.

The invention claimed is:

1. A method of treating gastrointestinal disorders related to the production of hydrogen in the gastrointestinal tract in a mammal, the method comprising administering to a mammal in need thereof a composition comprising *Ruminococcus hydrogenotrophicus* wherein said method does not remove any existing enteric microbial flora prior to administering said composition orally or rectally and wherein said composition modulates the balance of the microbial flora in the colon and reduces the amount of gaseous hydrogen produced by the existing flora.

2. The method of claim 1, wherein *Ruminococcus hydrogenotrophicus* remains active in the colon.

3. The method of claim 1, wherein the composition also comprises a pharmaceutically acceptable carrier.

4. The method of claim 1, wherein said mammal is human, canine or feline.

5. The method of claim 1, wherein said gastrointestinal disorder is selected from the group consisting of irritable bowel syndrome, excessive flatulence, meteorism, bloating and abdominal pain.

* * * * *